United States Patent [19]
Hamer et al.

[11] Patent Number: 4,883,794
[45] Date of Patent: Nov. 28, 1989

[54] PYRROLO(1,2-B)CINNOLINES

[75] Inventors: R. Russell L. Hamer, Far Hills; Richard C. Effland; Joseph T. Klein, both of Bridgewater, all of N.J.

[73] Assignee: Hoechst-Roussel Pharmaceuticals, Inc., Somerville, N.J.

[21] Appl. No.: 286,396

[22] Filed: Dec. 19, 1988

Related U.S. Application Data

[62] Division of Ser. No. 100,700, Sep. 24, 1987, Pat. No. 4,800,203.

[51] Int. Cl.$^4$ .................. A61D 31/50; C07D 487/04
[52] U.S. Cl. ..................................... 514/248; 544/235
[58] Field of Search ........................................ 514/248

[56] References Cited

U.S. PATENT DOCUMENTS 4,800,203 1/1989 Hamer et al. ...................... 514/248

Primary Examiner—Mukund J. Shah
Assistant Examiner—E. Bernhardt
Attorney, Agent, or Firm—Tatsuya Ikeda

[57] ABSTRACT

There are described pyrrolo[1,2-b] cinnolines having formula

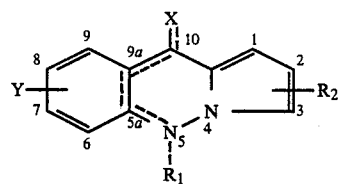

where $R_1$ when present is hydrogen, loweralky, aryl-loweralkyl or $-CH_2CO_2C_2H_5$; is hydrogen, loweralkyl, arylloweralkyl, chlorine, bromine, iodine, formyl, nitro, $-CH=CR_3R_4$ or $-CH_2CHR_3R_4$, $R_3$ and $R_4$ being independently hydrogen, loweralkyl, aryl or aryl-loweralkyl; X is oxygen, amino, loweralkylamino, aryl-loweralkylamino or methoxy; and Y is hydrogen, flourine, chlorine, bromine, iodine, trifluoromethyl or nitro, and pharmaceutically acceptable acid addition salts thereof which are useful as analgesic agents and as enhancers of cholinergic function and hence for the treatment of memory dysfunctions and senile demetia's such as Alzheimer's disease characterized by diminished cholinergic function.

1 Claim, No Drawings

PYRROLO(1,2-B)CINNOLINES

This is a division of a prior application, Ser. No. 100,700, filed Sept. 24, 1987, now U.S. Pat. No. 4,800,203.

The present invention relates to compounds of the formula

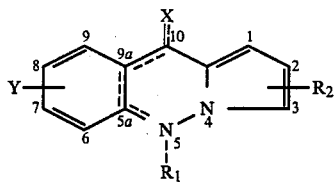

where $R_1$ when present is hydrogen, loweralkyl, aryl-loweralkyl or $-CH_2CO_2C_2H_5$; $R_2$ is hydrogen, loweralkyl, arylloweralkyl, chlorine, bromine, iodine, formyl, nitro, $-CH=CR_3R_4$ or $-CH_2CHR_3R_4$, $R_3$ and $R_4$ being independently hydrogen, loweralkyl, aryl or arylloweralkyl; X is oxygen, amino, loweralkylamino, arylloweralkylamino or methoxy; and Y is hydrogen, fluorine, chlorine, bromine, iodine, trifluoromethyl or nitro, and pharmaceutically acceptable acid addition salts thereof which are useful as analgesic agents and as enhancers of cholinergic function and hence for the treatment of memory dysfunctions and senile dementia's such as Alzheimer's disease characterized by diminished cholinergic function.

Throughout the specification and the appended claims, a given chemical formula or name shall encompass all stereo, optical, and geometrical isomers thereof where such isomers exist, as well as pharmaceutically acceptable acid addition salts thereof and solvates thereof such as for instance hydrates.

The following general rules of terminology shall apply throughout the specification and the appended claims.

Unless otherwise stated or indicated, the term loweralkyl denotes a straight or branched alkyl group having from 1 to 6 carbon atoms. Examples of said loweralkyl include methyl, ethyl, n-propyl, iso-propyl, n-butyl, iso-butyl, sec-butyl, t-butyl and straight- and branched-chain pentyl and hexyl.

Unless otherwise stated or indicated, the term loweralkoxy denotes a straight or branched alkoxy group having from 1 to 6 carbon atoms. Examples of said loweralkoxy include methoxy, ethoxy, n-propoxy, iso-propoxy, n-butoxy, iso-butoxy, sec-butoxy, t-butoxy, and straight- and branched-chain pentoxy and hexoxy.

Unless otherwise stated or indicated, the term aryl shall mean a phenyl group having 0, 1, 2 or 3 substituents each of which being independently loweralkyl, loweralkoxy, halogen, $CF_3$, $NO_2$ or $CN$.

The dotted lines appearing in formula I are optional bonds and shall signify the following facts:

When $R_1$ is present, namely, when the dotted line between nitrogen at 5-position and the group $R_1$ is a real bond, the dotted line between nitrogen at 5-position and carbon at 5a-position as well as the dotted line between carbon-9a and carbon-10 shall be null bonds, and the dotted line between carbon 5a and carbon 9a as well as the dotted line between carbon-10 and the group X shall be real bonds. Conversely, when $R_1$ is non-existent, the dotted line between nitrogen-5 and carbon-5a as well as the dotted line between carbon 9a and carbon 10 shall be real bonds, and the dotted line between carbon-5a and carbon-9a as well as the dotted line between carbon-10 and the group X shall be null bonds.

The compounds of formula I of this invention can be synthesized by utilizing one or more of the synthetic steps described below. Throughout the description of the synthetic steps, the definitions of $R_1$, $R_2$, $R_3$, $R_4$, X and Y are as given earlier unless otherwise specifically indicated.

STEP A

A compound of formula II where Hal is fluorine or chlorine is reacted with a compound of formula III (phthalimidopyrrole) to afford a compound of formula IV.

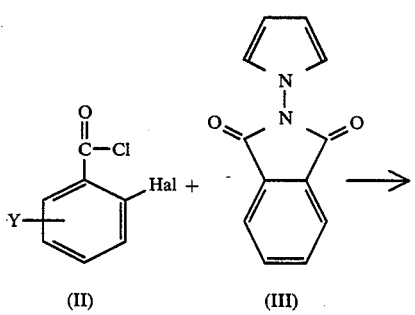

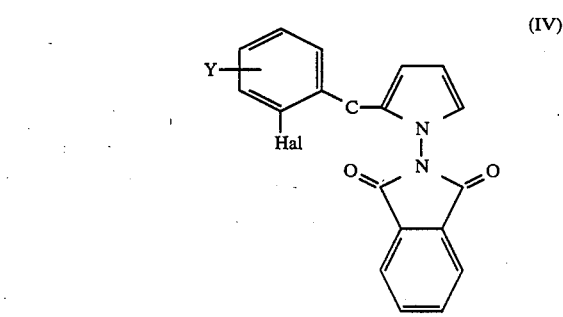

The above reaction is typically conducted in a suitable medium such as 1,2-dichloroethane and a suitable catalyst such as Montmorillonite clay or $ZnCl_2$ and stirring the reaction mixture at a temperature of about 25° C. to reflux temperature of the raction medium. Refluxing of the reaction medium is preferred.

STEP B

Compound IV is reacted with methylamine to afford a compound of formula V.

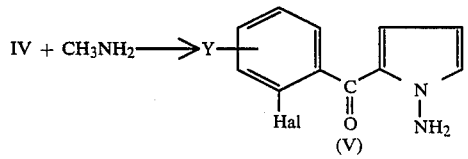

The above reaction is typically conducted by preparing a suspension of compound IV in a suitable medium such as ethanol, adding to the suspension an aqueous solution of methylamine and stirring the resultant mixture at a temperature of about 25° to 80° C.

STEP C

Compound V is reacted with ethyl chloroformate to afford a compound of formula VI.

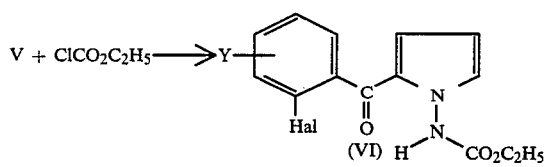

The above reaction is typically conducted in a suitable solvent such as dichloromethane in the presence of an acid scavenger such as sodium bicarbonate at a temperature of about 25° C. to reflux temperature of the reaction medium. Reflux condition of the solvent is preferred.

STEP D

Compound VI is reacted with loweralkyl iodide of the formula $R_5I$ where $R_5$ is loweralkyl to afford a compound of formula VII.

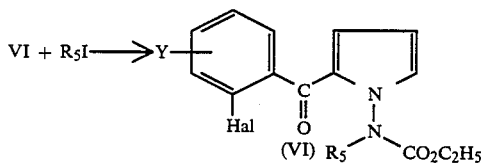

The above reaction is typically conducted in a suitable medium such as dimethylformamide in the presence of an acid scavenger such as potassium carbonate, sodium carbonate or the like at a temperature of 25° to 80° C.

STEP E

A compound of formula VIII where $R_6$ is hydrogen or loweralkyl which is obtained from STEP C or D is cyclized to afford a compound of formula IX.

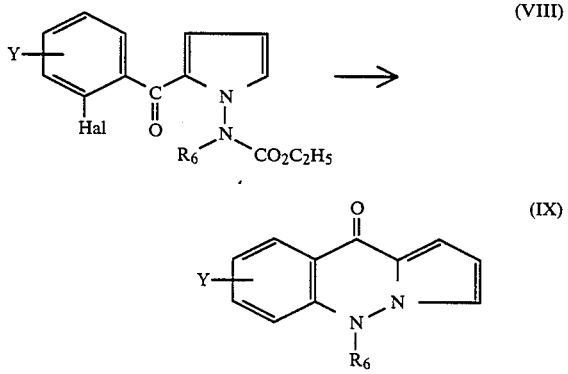

The above reaction is typically conducted with the aid of an inorganic base such as potassium hydroxide or sodium hydroxide in a suitable medium such as ethanol/water mixture at a temperature of 25° C. to reflux temperature of the reaction medium. Refluxing of the reaction medium is preferred.

STEP F

Compound IXa obtained from STEP E is reacted with a compound of formula X where $R_7$ is loweralkyl or arylloweralkyl and Z is Cl, Br, I or $OSO_2CH_3$ to afford a compound of formula XI.

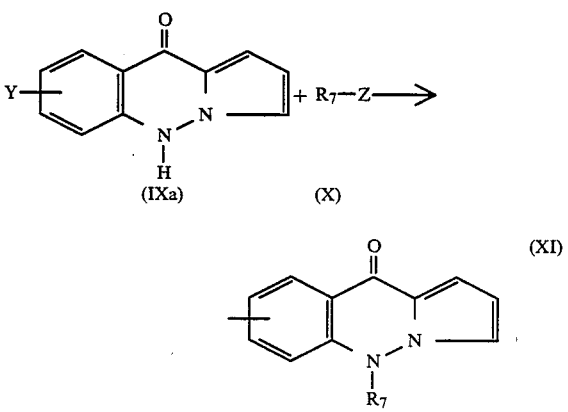

The above reaction is typically conducted in the presence of a suitable acid scavenger such as milled potassium carbonate in a suitable medium such as dimethylformamide or 2-butanone at a temperature of about 25° to 150° C., preferably 50° to 75° C.

STEP G

Compound IXa is reacted with ethyl bromoacetate to afford a compound of formula XII.

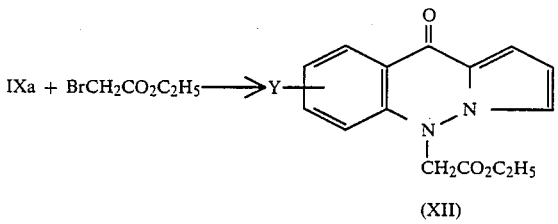

The above reaction is typically conducted in the presence of a suitable acid scavenger such as milled potassium carbonate in a suitable medium such as methyl ethyl ketone at a temperature of about 25° to 150° C., preferably 25° to 50° C.

STEP H

A compound of formula Ia obtained form STEP E, F or G is reacted with N-chlorosuccinimide (NCS), N-bromosuccinimide (NBS) or N-iodosuccinimide (NIS) in a routine manner known to the art to afford a compound of formula Ib, Ic or Id, respectively.

In these reactions, the halogenation occurs on the pyrrole moiety of the 3-ring system. The positional isomers can be separated by methods known in the art such as high performance liquid chromatography (HPLC).

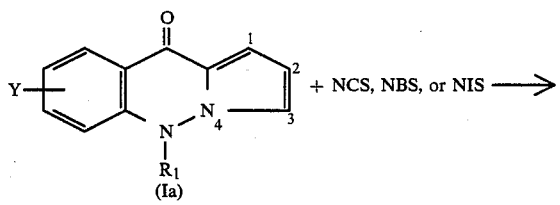

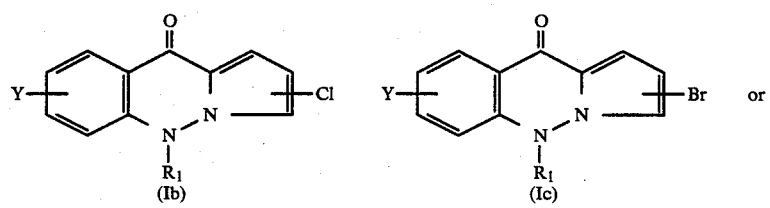

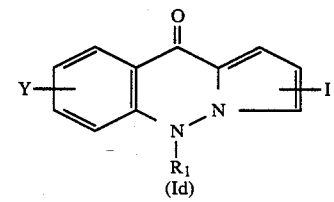

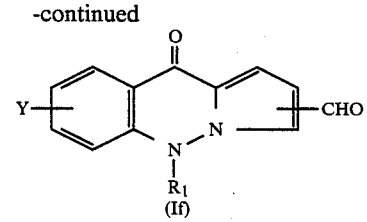

-continued

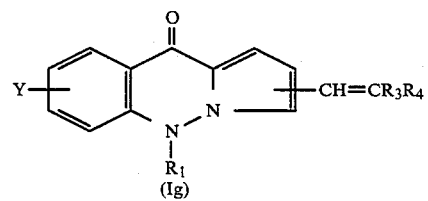

STEP I

Compound Ia is reacted with silver nitrate and acetyl chloride to afford a compound of formula Ie. The positional isomers can be separated by methods known in the art such as HPLC.

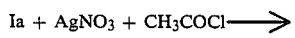

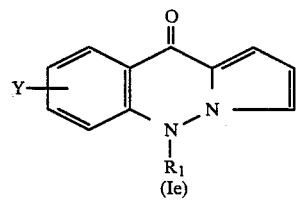

The above reaction is typically conducted in a suitable medium such as acetonitrile at a temperature of about 0° to 80° C.

STEP J

Compound Ia is reacted with phosphorus oxychloride and dimethylformamide to afford a compound of formula If (Vilsmeier reaction). The positional isomers can be separated by methods known in the art such as HPLC.

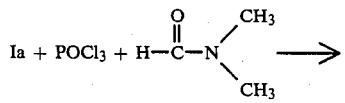

The above reaction can be conducted under conditions usually used for carrying out Vilsmeier reactions. Typically, it is conducted in a suitable solvent such as halogenated hydrocarbon at a temperature of about 20°–100° C.

STEP K

Compound If is subjected to Wittig reaction with an ylide of the formula $(C_6H_5)_3P=CR_3R_4$ where $R_3$ and $R_4$ are as defined earlier to afford a compound of formula Ig.

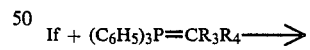

The above reaction can be conducted under conditions usually used for carrying out Wittig reactions. Thus, the ylide is prepared in a routine manner by first preparing a phosphonium salt from a halide of the formula $WCHR_3R_4$ where $W=Br$, Cl or I and triphenylphosphine and thereafter reacting the phosphonium salt with a suitable base such as sodium hydride, potassium tert-butoxide or n-butyllithium in a suitable solvent such as an anhydrous ether. Thereafter a solution of compound If in a suitable solvent such as an anhydrous ether is added to the freshly prepared ylide solution and the mixture is stirred at a temperature of between about −10° C. and 80° C.

STEP L

Compound Ig is catalytically hydrogenated in a suitable manner known to the art to afford a compound of formula Ih.

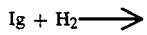

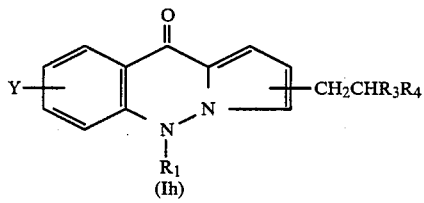

STEP M

A compound of formula Ii obtained from one of the foregoing STEPS is reacted with diazomethane to afford a compound of formula Ij.

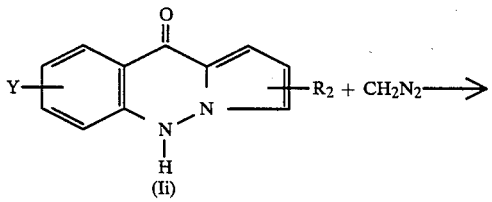

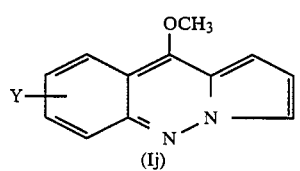

Typically, a solution of diazomethane in ether is prepared in a routine manner known to the art and the solution is added to a mixture of compound Ii and a suitable medium such as tetrahydrofuran. The reaction is conducted by stirring the resultant mixture at a temperature of about 0° to 50° C.

STEP N

Compound Ij is reacted with a compound of the formula $H_2NR_8$ where $R_8$ is hydrogen, loweralkyl or arylloweralkyl to afford a compound of formula Ik.

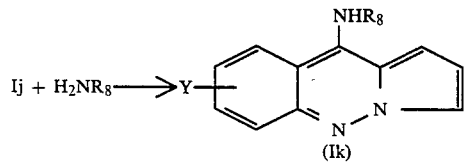

This reaction is typically conducted in a suitable medium such as anhydrous benzene and in the presence of a suitable catalyst such as mercury (II) acetate at a temperature of 25° to 80° C.

Compounds of formula I of the present invention are useful as analgesic agents due to their ability to alleviate pain in mammals. The activity of the compounds is demonstrated in the 2-phenyl-1,4-benzoquinone-induced writhing (PQW) test in mice, a standard assay for analgesia [Proc. Soc. Exptl. Biol. Med., 95, 729 (1957)].

The results of some of the compounds of this invention are shown in Table 1 along with that of a reference compound.

TABLE 1

ANALGESIC ACTIVITY PQW

| Compound | Inhibition of % Writhing | Dose, mg/kg sc |
|---|---|---|
| 5-Methylpyrrolo[1,2-b]-cinnolin-10(5H)-one | 30 | 20 |
| 3-Chloro-5-methylpyrrolo-[1,2-b]cinnolin-10(5H)-one | 33 | 20 |
| 10-Oxopyrrolo[1,2-b]cinnolin acetic acid, ethyl ester | 51 | 20 |
| 5-Benzylpyrrolo[1,2-b]-cinnolin-10(5H)-one (Reference Compound) | 49 | 20 |
| propoxyphene | 50 | 3.9 |

The compounds of formula I of the invention are also useful in the treatment of various memory dysfunctions characterized by decreased cholinergic function, such as Alzheimer's disease.

This utility is demonstrated by the ability of these compounds to restore cholinergically deficient memory in the Dark Avoidance Assay, where they are generally active over a broader dose range than heretofore known compounds, a distinct therapeutic advantage.

Dark Avoidance Assay (reference: Z. Bohdanecky & M. E. Jarvik, Int. J. Neuropharmacol. 6 217 (1967))

In this assay mice are tested for their ability to remember an unpleasant stimulus for a period of 24 hours. A mouse is placed in a chamber that contains a dark compartment; a strong incandescent light drives it to the dark compartment, where an electric shock is administered through metal plates on the floor. The animal is removed from the testing apparatus and tested again, 24 hours later, for the ability to remember the electric shock.

If scopolamine, an anticholinergic that is known to cause memory impairment, is administered before an animals' initial exposure to the test chamber, the animal re-enters the dark compartment shortly after being placed in the test chamber 24 hours later. This effect of scopolamine is countered by an active test compound, resulting in a greater interval before re-entry into the dark compartment.

The results for active compound are expressed as the percent of a group of animals in which the effect of scopolamine is countered, as manifested by an increased interval between being placed in the test chamber and re-entering the dark compartment.

The results of a representative compound of this invention are presented in Table 2 along with that of physostigmine, a reference compound.

TABLE 2

| Compound | Dose mg/kg Body Weight s.c | % of Animals With Scopolamine Induced Memory Deficit Reversed |
|---|---|---|
| 10-Oxopyrrolo[1,2-b]-cinnolin acetic acid, | 1.25 | 20% |

TABLE 2-continued

| Compound | Dose mg/kg Body Weight s.c | % of Animals With Scopolamine Induced Memory Deficit Reversed |
|---|---|---|
| ethyl ester (Reference Compound) | | |
| Physostigmine | 0.31 | 20% |

Further evidence of cholinergic activity (cholinomimetic) is provided by a compound's ability to produce a contraction in an isolated guinea pig ileum preparation (reference: J. P. Long and C. Y. Chiou, J. Pharmaceutical Sci., 59 133 (1970)).

The method is described below.

METHOD

Male guinea pigs weighing 350 grams or more are utilized (the weight or food deprivation is not critical to experimental results). The animal is stunned by a blow to the head and exsanguinated. The abdomen is opened and a segment of ileum (10 to 15 cm) proximal to the ileocecal function is removed (A. F. Munro, J. Physiology, 112 84 (1951) and placed in a culture dish and immersed with Krebs solution. Sections of ileum are then cut 3 cm in length and thoroughly rinsed.

The rinsed segment is slid onto the thick section of a Pasteur pipette. Using a wet Q-tip with Krebs, the tissue is stroked tangentially into the mesentary border along the length of the segment. Gradually, the thin grey longitudinal muscle will pull away. Continue stroking tangentially all around the segment. The longitudinal muscle will easily pull away upon completion. If there is any resistance, cut along the mesentary border. The strip is then placed in clean Krebs solution. Four-O silk is secured to each end making a 1.5 to 2 cm strip. The strip is then ready for hanging in the bath bubbled with 95% $O_2$ and 5% $CO_2$. The bath temperature is maintained at 37° C. About 0.5 to 1.0 gram of tension is applied and the tissue is left to equilibrate for one hour.

When testing for cholinergic compounds, the tissues are challenged with acetylcholine chloride at $2.7 \times 10^{-5}$M after one hour. The response must be greater than seven decigrams. A tissue cannot be used if the response to acetylcholine is equal to or less than seven decigrams. N=3 tissues will be recognized to be taken from one or more guinea pigs.

The Krebs bicarbonate solution is made in the following manner and chlorpheniramine is added to antagonize endogenous histamine:

| Compound | Final Concentration | 4 L Stock Sol. |
|---|---|---|
| NaCl | 118 mM | 276 grams |
| KCl | 4.7 mM | 14.0 grams |
| $CaCl_2$ | 2.54 mM | 14.8 grams |
| $KH_2PO_4$ | 1.2 mM | 6.4 grams |
| $MgSO_4.7H_2O$ | 1.2 mM | 5.6 grams |
| $NaHCO_3$ | 25.0 mM | * |
| Glucose | 11.5 mM | * |
| Chlorpheniramine | $1.25 \times 10^{-6}$ M | 1.92 mg |

*To each 100 mls of stock solution add 2.0 grams of glucose and 2.1 grams of $NaHCO_3$ and QS to 1000 mls, with distilled $H_2O$.

Results of representative compounds of this invention are presented in Table 3.

TABLE 3

| Compound | Guinea Pig Ileum % Contraction at [M] Concentration |
|---|---|
| 5-Methylpyrrolo[1,2-b]-cinnolin-10(5H)-one | 52% at $7.2 \times 10^{-4}$ M |
| 3-Chloro-5-methylpyrrolo-[1,2-b]cinnolin-10(5H)-one | 50% at 1.2 $10^{-6}$ |
| 10-Oxopyrrolo[1,2-b]cinnolin acetic acid, ethyl ester | 50% at $2.4 \times 10^{-5}$ |
| 7-Chloro-5-propylpyrrolo[1,2-b]-cinnolin-10(5H)-one (Reference Compound) | 25% at 8.1 at $10^{-5}$ |
| carbachol | 50% at $1.3 \times 10^{-7}$ |

Examples of the compounds of this invention include:
pyrrolo[1,2-b]cinnolin-10(5H)-one;
7-chloropyrrolo[1,2-b]cinnolin-10(5H)-one;
5-methylpyrrolo[1,2-b]cinnolin-10(5H)-one;
7-chloro-5-methylpyrrolo[1,2-b]cinnolin-10(5H)-one;
7-chloro-5-propylpyrrolo[1,2-b]cinnolin-10(5H)-one;
5-benzylpyrrolo[1,2-b]cinnolin-10(5H)-one;
5-benzyl-7-chloropyrrolo[1,2-b]cinnolin-10(5H)-one;
10-oxopyrrolo[1,2-b]cinnolin acetic acid, ethyl ester;
3-chloro-5-methylpyrrolo[1,2-b]cinnolin-10(5H)-one;
3,7-dichloro-5-methylpyrrolo[1,2-b]cinnolin-10(5H)-one;
5-benzyl-3,7-dichloropyrrolo[1,2-b]cinnolin-10(5H)-one;
3-bromo-5-methylpyrrolo[1,2-b]cinnolin-10(5H)-one;
3-bromo-7-chloro-5-methylpyrrolo[1,2-b]cinnolin-10(5H)-one;
5-benzyl-3-bromo-7-chloropyrrolo[1,2-b]cinnolin-10(5H)-one;
5-methyl-3-nitropyrrolo[1,2-b]cinnolin-10(5H)-one;
7-chloro-10-methoxypyrrolo[1,2-b]cinnoline; and
N-benzyl-7-chloropyrrolo[1,2-b]cinnolin-10-amine.

The following examples are presented in order to illustrate this invention.

EXAMPLE 1

2-(2,4-Dichlorobenzoyl)-1-phthalimidopyrrole

To a suspension of phthalimidopyrrole (748.6 g) and 2,4-dichlorobenzoyl chloride (1109.1 g) in 3.5 L of dichloroethane was added 707.3 g of K-10 Montmorillonite clay. The resulting mixture was stirred at reflux for 48 hrs, then filtered and concentrated to a semisolid. The semisolid was triturated with a large quantity of ether and collected to yield 1112.5 g of powder. The ether wash was concentrated to give 162.0 of a residue. This was purified by high performance liquid chromatography (HPLC hereinafter, silica, dichloromethane) and recrystallized from absolute ethanol to yield 37.26 g of crystals, mp 152°–153° C.

ANALYSIS: Calculated for $C_{19}H_{10}Cl_2N_2O_3$: 59.24%C; 2.62%H; 7.27%N; Found: 59.25%C; 2.74%H; 7.41%N.

EXAMPLE 2

1-Amino-2-(2,4-dichlorobenzoyl)pyrrole hydrochloride

A suspension of 2-(2,4-dichlorobenzoyl)-1-phthalimidopyrrole (1112.5 g) in 3 L of 95% ethanol was treated with 1.5 L of 40% aqueous solution of methylamine and stirred at room temperature for 4 h. The reaction mixture was quenched with 5 L of $H_2O$ an extracted with three 500 ml portions of dichloromethane. The combined dichloromethane extracts were washed with $H_2O$, dried ($MgSO_4$), filtered and concentrated to an orange oil. The orange oil was distilled to give a yellow oil which crystallized to yield 448.6 g of off-white crystals. A 71.0 g portion of the crystals was further purified by HPLC (silica, dichloromethane) and concentrated to give 50.2 g of a yellow oil which was taken up in ether and treated with ether saturated with HCl. A light tan powder fell out of the solution which was recrystallized from ethanol to yield 22.1 g of tan microcrystals, mp 164°–167° C.

ANALYSIS: Calculated for $C_{11}H_8Cl_2N_2O \cdot HCl$: 45.31%C; 3.11%H; 9.61%N; Found: 45.24%C; 3.12%H; 9.62%N.

EXAMPLE 3

[2-(2,4-Dichlorobenzoyl)-1H-pyrrol-1-yl]carbamic acid, ethyl ester

To a stirred slurry of 1-amino-2-(2,4-dichlorobenzoyl)pyrrole (377.6 g) and sodium bicarbonate (286.0 g) in 2.0 L of dichloromethane was added ethyl chloroformate (176.90 g) over 10 min. The reaction mixture was heated at reflux for 4 hrs and then quenched with $H_2O$. The organic layer was washed with brine, dried ($MgSO_4$), charcoaled, filtered and concentrated to a maroon oil. This oil was purified by flash chromatography (silica, dichloromethane) and concentrated to a green powder which was recrystallized from ether to give 171.8 g of white crystals, mp 114°–116°.

ANALYSIS: Calculated for $C_{14}H_{12}Cl_2N_2O_3$: 51.39%C; 3.70%H; 8.56%N; Found: 51.49%C; 3.82%H; 8.55%N.

EXAMPLE 4

[2-(2,4-Dichlorobenzoyl)-1H-pyrrol-1-yl]methyl carbamic acid, ethyl ester

Methyl iodide (56.78 g) was added over 15 min to a stirred slurry of [2-(2,4-dichlorobenzoyl)-1H-pyrrol-1-yl]carbamic acid, ethyl ester (64.50 g) and potassium carbonate (55.28 g) in 150 ml of dimethylformamide (DMF, hereinafter). The reaction mixture was stirred at room temperature for 4 hours after which the reaction was shown to be complete by G.C. It was then quenched with $H_2O$ and extracted with dichloromethane. The organic layer was washed with $H_2O$ and brine, dried over $MgSO_4$, charcoaled, filtered and concentrated. The resulting yellow oil crystallized overnight and was triturated with hexane to yield 50.79 g of white crystals, mp 79°–80°.

ANALYSIS: Calculated for $C_{15}H_{14}Cl_2N_2O_3$: 52.80%C; 4.14%H; 8.21%N; Found: 52.72%C; 4.16%H; 8.07%N.

EXAMPLE 5

Pyrrolo[1,2-b]cinnolin-10(5H)-one

A solution of [2-(2-fluorobenzoyl)-1H-pyrrol-1-yl]carbamic acid, ethyl ester (60.0 g, prepared from 1-amino-2-(2-fluorobenzyl)pyrrole and ethyl chloroformate in substantially the same manner as in Example 3) in 250 ml of ethanol was treated with a solution of potassium hydroxide (51 g) in 150 ml of water and then the mixture was heated at reflux for 1 hour. The ethanol was evaporated and the aqueous layer washed with 3×500 ml of ether. The aqueous phase was then adjusted to pH 5 with 6N HCl and the product collected by filtration. Oven drying yielded 20 g of a yellow powder, mp>300° C.

EXAMPLE 6

7-Chloropyrrolo[1,2-b]cinnolin-10(5H)-one

A solution of [2-(2,4-dichlorobenzoyl)-1H-pyrrol-1-yl]carbamic acid, ethyl ester (102.4 g) in 500 ml of ethanol was treated with a solution of potassium hydroxide (84 g) in 200 ml of water and then the mixture was stirred under reflux for 1 hour. The ethanol was evaporated and the aqueous layer was washed with 3×500 ml of ether. The aqueous phase was then adjusted to pH 5 with 6N HCl and the product collected by filtration. Oven drying yielded 68 g of a yellow green powder, mp>300° C.

EXAMPLE 7

5-Methylpyrrolo[1,2-b]cinnolin-10(5H)-one

A solution containing [2-(2-fluorobenzoyl)-1H-pyrrol-1-yl]methylcarbamic acid, ethyl ester (23.5 g, prepared from [2-(2-fluorobenzoyl)-1H-pyrrol-1-yl]carbamic acid, ethyl ester and methyl iodide in substantially the same manner as in Example 4) and sodium hydroxide (12.0 g) in 140 mL of 50% aqueous ethanol was refluxed under $N_2$ for 16 h. Evaporation of the volatiles left a bright yellow solid which was diluted with 300 ml of $H_2O$ and extracted with two 200 mL portions of dichloromethane. The organic extracts were dried ($MgSO_4$), filtered and concentrated. The residue was recrystallized from dichloromethane to give 8.0 g of bright yellow crystals, mp 154°–156° C.

ANALYSIS: Calculated for $C_{12}H_{10}N_2O$: 72.70%C; 5.08%H; 14.13%N; Found: 72.36%C; 5.33%H; 14.08%N.

EXAMPLE 8

7-Chloro-5-methylpyrrolo[1,2-b]cinnolin-10(5H)-one

To a refluxing slurry of [2-(2,4-dichlorobenzoyl)-1H-pyrrol-1-yl]methyl carbamic acid, ethyl ester (25.11 g) in 500 ml of ethanol was added a solution of potassium hydroxide (68.3 g) in 68 ml of $H_2O$. The mixture was stirred at reflux for 5 hours and then concentrated to an orange oil. Water was added to the oil producing a yellow precipitate. This powder was collected and recrystallized first from methanol and then from ethanol to yield 6.63 g of yellow microcrystals, mp 172°–173°.

ANALYSIS: Calculated for $C_{12}H_9ClN_2O$: 61.67%C; 4.31%H; 11.99%N; Found: 62.06%C; 3.97%H; 12.12%N.

EXAMPLE 9

7-Chloro-5-propylpyrrolo[1,2-b]cinnolin-10(5H)-one

7-Chloropyrrolo[1,2-b]cinnolin-10(5H)-one (9.0 g) was taken up in 100 ml of DMF and milled $K_2CO_3$ (11.33 g) was added. 1-Bromopropane (10.09 g) was then added dropwise and the solution was stirred at room temperature for 48 h. Water was added and the solution was extracted into dichloromethane and washed several times with $H_2O$ and dilute hydrochloric acid. The organics were then dried ($MgSO_4$), charcoaled, filtered and concentrated to an orange oil. The oil was purified by HPLC (silica, dichloromethane) and concentrated to give 6.33 g of an orange powder which was recrystallized from ether to yield 3.4 g of yellow-orange microcrystals, mp 107°–108°.

ANALYSIS: Calculated for $C_{14}H_{13}ClN_2O$: 64.49%C; 5.02%H; 10.75%N; Found: 64.59%C; 4.99%H; 10.72%N.

EXAMPLE 10

5-Benzylpyrrolo[1,2-b]cinnolin-10(5H)-one

A stirred slurry containing pyrrolo[1,2-b]cinnolin-10(5H)-one (4.0 g) and potassium carbonate (11.2 g) in 100 ml of 2-butanone was treated with benzyl bromide (4.0 g) and the mixture was stirred at 60°. After 4 h the mixture was quenched with 700 ml of H$_2$O and extracted with two 150 ml portions of dichloromethane. These organic extracts were dried over MgSO$_4$, filtered and concentrated to a green oil. This oil was purified by flash chromatography (silica, dichloromethane) to a yellow solid which was recrystallized from dichloromethane to give 3.5 g of bright yellow crystals, mp 146°–148°.

ANALYSIS: Calculated for C$_{18}$H$_{14}$N$_2$O: 78.80%C; 5.14%H; 10.21%N; Found: 79.10%C; 5.38%H; 10.40%N.

EXAMPLE 11

5-Benzyl-7-chloropyrrolo[1,2-b]cinnolin-10(5H)-one

To a slurry of 7-chloropyrrolo[1,2-b]cinnolin-10(5H)-one (35.0 g) and potassium carbonate (66.34 g) in 150 ml of 2-butanone was added benzyl bromide (44.47 g) and the mixture was stirred at 50° for 2 h. The reaction was quenched with 750 ml of H$_2$O, and the mixture was neutralized with 2N HCl to pH 8 and extracted with chloroform. The organic layer was washed successively with dilute HCl, H$_2$O and brine and thereafter dried (MgSO$_4$), charcoaled, filtered and concentrated. The yellow-orange residue was purified by flash chromatography (silica, dichloromethane) and recrystallized from ethanol to give 12.0 g of light yellow microcrystals, mp 163°–165°.

ANALYSIS: Calculated for C$_{18}$H$_{13}$ClN$_2$O: 70.02%C; 4.24%H; 9.08%N; Found: 70.07%C; 4.31%H; 9.15%N.

EXAMPLE 12

10-Oxopyrrolo[1,2-b]cinnolin acetic acid, ethyl ester

To a solution of pyrrolo[1,2-b]cinnolin-10(5H)-one (11.70 g) in 100 ml of methyl ethyl ketone was added potassium carbonate (26.54 g) and then ethyl bromoacetate (10.69 g). The solution was stirred at room temperature for 3 hours and then concentrated. The residue was dissolved in 1 L of dichloromethane and filtered through a celite pad to give a deep orange solution which was washed with H$_2$O and brine. The organic layer was then dried (MgSO$_4$), charcoaled, filtered and concentrated to give 12.03 g of an orange powder. A 3.5 gram portion of the powder was purified by flash chromatography (silica, dichloromethane) and recrystallized from absolute EtOH to yield 2.2 g of light yellow microcrystals, mp 129°–131°.

ANALYSIS: Calculated for C$_{15}$H$_{14}$N$_2$O$_3$: 66.65%C; 5.22%H; 10.37%N; Found: 66.35%C; 5.36%H; 10.41%N.

EXAMPLE 13

3-Chloro-5-methylpyrrolo[1,2-b]cinnolin-10(5H)-one

A solution of 5-methylpyrrolo[1,2-b]cinnolin-10(5H)-one (5.0 g) in 180 mL of tetrahydrofuran at 0° C. was treated with N-chlorosuccinimide (3.4 g) all at once and the mixture was stirred at ambient temperature. After 36 h the solution was concentrated and the residue taken up in chloroform. This solution was washed with two 100 ml portions of water, dried over MgSO$_4$, filtered and concentrated. The residue was purified by flash chromatography (silica, dichloromethane) to give 2.83 g of an off-white powder, mp 88.5°–90.5° C.

ANALYSIS: Calculated for C$_{12}$H$_9$ClN$_2$O: 61.94%C; 3.89%H; 12.04%N; Found: 61.69%C; 4.05%H; 12.14%N.

EXAMPLE 14

3,7-Dichloro-5-methylpyrrolo[1,2-b]cinnolin-10(5H)-one

To a solution containing 7-chloro-5-methylpyrrolo[1,2-b]cinnolin-10(5H)-one (3.0 g) and a catalytic amount of dibenzoyl peroxide in 50 ml of THF was added portionwise N-chlorosuccinimide (1.74 g) over 15 min. The flask was covered with aluminum foil and the solution stirred at room temperature for 24 hrs. The solution was then concentrated and the residue purified by HPLC (silica, dichloromethane) to give 2.43 g of a yellow powder. This powder was recrystallized from ethanol to give 2.23 g of pale yellow crystals, mp 129°–131°.

ANALYSIS: Calculated for C$_{12}$H$_8$Cl$_2$N$_2$O: 53.95%C; 3.02%H; 10.49%N; Found: 53.96%C; 2.94%H; 10.46%N.

EXAMPLE 15

5-Benzyl-3,7-dichloropyrrolo[1,2-b]cinnolin-10(5H)-one

5-Benzyl-7-chloropyrrolo[1,2-b]cinnolin-10(5H)-one (4.5 g) was taken up in 50 ml of THF and a catalytic amount of dibenzoyl peroxide was added. N-chlorosuccinimide (1.95 g) was added portionwise over a period of 10 min. The flask was covered with aluminum foil and the mixture stirred at room temperature overnight under N$_2$. The reaction mixture was concentrated and the residue taken up in chloroform and extracted with H$_2$O and brine. The organic layer was then dried (MgSO$_4$), charcoaled, filtered and concentrated to a green semisolid. This was purified by HPLC (silica, dichloromethane) to give a light green powder which was recrystallized from ethanol to yield 2.3 g of green crystals, mp 134°–136°.

ANALYSIS: Calculated for C$_{18}$H$_{12}$Cl$_2$N$_2$O: 62.80%C; 3.51%H; 8.14%N; Found: 62.99%C; 3.58%H; 8.13%N.

EXAMPLE 16

3-Bromo-5-methylpyrrolo[1,2-b]cinnolin-10(5H)-one

A solution of N-bromosuccinimide (3.5 g) in 50 mL of THF was added dropwise to a solution of 5-methylpyrrolo[1,2-b]cinnolin-10(5H)-one (3.8 g) in 70 mL of dry THF at 0° C. After 16 hours of stirring at room temperature, the solution was concentrated and the residue taken up in 200 mL of CHCl$_3$. This solution was washed with H$_2$O, dried over MgSO$_4$, filtered and concentrated. The residue was purified by HPLC (silica, dichloromethane) to give 3.8 g of yellow crystals. This material was recrystallized from ether to give 3.6 g of pale yellow crystals, mp 103°–105° C.

ANALYSIS: Calculated for C$_{12}$H$_9$BrN$_2$O: 52.00%C; 3.27%H; 10.11%N; Found: 51.61%C; 3.30%H; 10.17%N.

EXAMPLE 17

3-Bromo-7-chloro-5-methylpyrrolo[1,2-b]cinnolin-10(5H)-one

To a solution of 7-chloro-5-methylpyrrolo[1,2-b]cinnolin-10(5H)-one (6.0 g) and a catalytic amount of dibenzoyl peroxide in 100 ml of THF was added portionwise N-bromosuccinimide (4.63 g) over 15 min. The flask was covered with aluminum foil and the solution was stirred at room temperature for 24 hrs. The solution was then concentrated and the residue was purified by HPLC (silica, dichloromethane) to give 7.10 g of a light green powder. This powder was recrystallized from ethanol to give 5.7 g of a yellow fibrous material, mp 133°–135°.

ANALYSIS: Calculated for $C_{12}H_8BrClN_2O$: 46.26%C; 2.59%H; 9.03%N; Found: 46.31%C; 2.81%H; 9.03%N.

EXAMPLE 18

5-Benzyl-3-bromo-7-chloropyrrolo[1,2-b]cinnolin-10(5H)-one

5-Benzyl-7-chloropyrrolo[1,2-b]cinnolin-10(5H)-one (4.5 g) was taken up in 50 ml of THF and a catalytic amount of dibenzoyl peroxide was added portionwise over a period of 10 min. The flask was covered with aluminum foil and the mixture stirred at room temperature overnight under $N_2$. The reaction mixture was concentrated and the residue taken up in chloroform and extracted with $H_2O$ and brine. The organic layer was then dried ($MgSO_4$), charcoaled, filtered and concentrated to a green semisolid. This was purified by HPLC (silica, dichloromethane) to give a light green powder which was recrystallized from ethanol to yield 3.75 g of a light yellow fibrous material, mp 148°–149°.

ANALYSIS: Calculated for $C_{18}H_{12}BrClN_2O$: 55.62%C; 3.11%H; 7.21%N; Found: 55.88%C; 3.13%H; 7.10%N.

EXAMPLE 19

5-Methyl-3-nitropyrrolo[1,2-b]cinnolin-10(5H)-one

To a solution of 5-methylpyrrolo[1,2-b]cinnolin-10(5H)-one (3.0 g) in 50 ml of acetonitrile was added silver nitrate (2.55 g) and the solution was cooled to 0° C. Acetyl chloride (1.18 g) was then added dropwise. After 2 hours the reaction mixture was added to 500 ml of ice water and filtered to yield 4.8 g of a yellow powder. Recrystallization from acetonitrile gave 3.0 g of bright yellow crystals, mp 263°.

ANALYSIS: Calculated for $C_{12}H_9N_3O_3$: 59.25%C; 3.73%H; 17.28%N; Found: 59.51%C; 3.49%H; 17.42%N.

EXAMPLE 20

7-Chloro-10-methoxypyrrolo[1,2-b]cinnoline

Diazomethane was prepared by adding Diazald ® (21.4 g) in 200 ml of ether to potassium hydroxide (5.0 g) in 20 ml of 50% ethanol/water solution and then distilling. This procedure was followed three times to give a solution of diazomethane (16.25 g) in ether which was then added to a stirred slurry of 7-chloropyrrolo[1,2-b]cinnolin-10(5H)-one (37.0 g) in 250 ml of tetrahydrofuran. The mixture was allowed to stand at room temperature for 48 hours and then the volatiles were removed. The residue was taken up in dichloromethane and washed several times with water. The organic layer was dried ($MgSO_4$), filtered and concentrated to a dark orange powder. The powder was purified by flash chromatography (silica, dichloromethane) to give 18.35 g of an orange powder. A five gram portion of this powder was recrystallized from ether to give 4.3 g of an orange fibrous material, mp 128°–129°.

ANALYSIS: Calculated for $C_{12}H_9ClN_2O$: 61.94%C; 3.90%H; 12.04%N; Found: 61.94%C; 3.80%H; 11.94%N.

EXAMPLE 21

N-Benzyl-7-chloropyrrolo[1,2-b]cinnolin-10-amine

A slurry of 7-chloro-10-methoxypyrrolo[1,2-b]cinnoline (8.1 g) and benzylamine (107 g) in 80 ml of dry benzene was treated with mercury(II) acetate (1.7 g). After 1 hour the mixture was heated at 55° for 2.5 hours and then concentrated under high vacuum. The residue was triturated with 50 ml of cold ether and collected. The orange powder thus obtained was recrystallized from hot ether to give 9.7 g of an orange powder, mp 184°-186° C.

ANALYSIS: Calculated for $C_{18}H_{14}ClN_3$: 70.24%C; 4.58%H; 13.65%N; Found: 70.20%C; 4.52%H; 13.62%N.

We claim:

1. A method of treating a patient in need of relief from a memory dysfunction characterized by decreased cholinergic function which comprises administering to the patient an effective amount of a compound having the formula

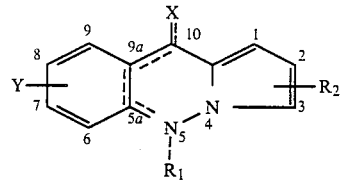

where $R_1$ when present is hydrogen, loweralkyl, aryloweralkyl or $-CH_2CO_2C_2H_5$; $R_2$ is hydrogen, loweralkyl, arylloweralkyl, chlorine, bromine, iodine, formyl, nitro, $-CH=CR_3R_4$ or $-CH_2CHR_3R_4$, $R_3$ and $R_4$ being independently hydrogen, loweralkyl, aryl or arylloweralkyl; X is oxygen, amino, loweralkylamino, arylloweralkylamino or methoxy; and Y is hydrogen, fluorine, chlorine, bromine, iodine, trifluoromethyl or nitro, the term aryl in each occurrence signifying a phenyl group having 0, 1, 2 or 3 substituents each of which being independently loweralkyl, loweralkoxy, halogen, $CF_3$, $NO_2$ or $CN$; or a pharmaceutically acceptable acid addition salt thereof.

* * * * *